United States Patent [19]

Butter

[11] 4,080,396
[45] Mar. 21, 1978

[54] SELECTIVE PRODUCTION OF PARA-XYLENE BY CONVERSION OF OLEFINS

[75] Inventor: Stephen A. Butter, East Windsor, N.J.

[73] Assignee: Mobil Oil Corporation, New York, N.Y.

[21] Appl. No.: 719,297

[22] Filed: Aug. 31, 1976

Related U.S. Application Data

[62] Division of Ser. No. 634,992, Nov. 24, 1975, Pat. No. 4,007,231.

[51] Int. Cl.² .................. C07C 3/02; C07C 15/08; B01J 29/36
[52] U.S. Cl. .................. 260/673; 208/135; 252/434; 252/456; 260/673.5
[58] Field of Search .................. 260/673, 673.5; 208/135

[56] References Cited

U.S. PATENT DOCUMENTS

| | | | |
|---|---|---|---|
| 3,711,422 | 1/1973 | Johnson et al. | 252/414 |
| 3,756,942 | 9/1973 | Cattanach | 208/137 |
| 3,760,024 | 9/1973 | Cattanach | 260/673 |
| 3,890,218 | 6/1975 | Morrison | 208/135 |
| 3,965,208 | 6/1976 | Butter et al. | 260/671 M |
| 4,025,458 | 5/1977 | McKay | 208/120 X |

Primary Examiner—Delbert E. Gantz
Assistant Examiner—G. E. Schmitkons
Attorney, Agent, or Firm—Charles A. Huggett; Raymond W. Barclay

[57] ABSTRACT

A catalytic process is provided for the selective production of para-xylene by contacting, under conversion conditions, a charge stock containing, as a major reactant, at least one hydrocarbon selected from the group consisting of toluene, a $C_3$-$C_{10}$ olefin, a $C_5$-$C_{10}$ naphthene, a $C_3$-$C_{10}$ paraffin, and mixtures of the foregoing with a catalyst comprising a composite of a crystalline aluminosilicate zeolite and antimony oxide, said zeolite having a silica to alumina ratio of at least about 12 and a constraint index, as hereinafter defined, within the approximate range of 1 to 12.

8 Claims, No Drawings

SELECTIVE PRODUCTION OF PARA-XYLENE BY CONVERSION OF OLEFINS

This application is a division of application Ser. No. 634,992, filed Nov. 24, 1975, now U.S. Pat. No. 4,007,231.

BACKGROUND OF THE INVENTION

1. Field of the Invention

This invention relates to a process for converting certain hydrocarbons to a high yield of para-xylene utilizing an antimony oxide-containing crystalline aluminosilicate zeolite catalyst.

2. Description of the Prior Art

The disproportionation of aromatic hydrocarbons in the presence of zeolite catalysts has been described by Grandio et al. in the Oil and Gas Journal, Vol. 69, No. 48 (1971).

U.S. Pat. Nos. 3,126,422; 3,413,374; 3,598,878; 3,598,879 and 3,607,961 show vapor-phase disproportionation of toluene over various catalysts.

Alkylation of aromatic hydrocarbons with an olefin in the presence of a crystalline metallic aluminosilicate having uniform pore openings of about 6 to 15 Angstrom units is described in U.S. Pat. No. 2,290,607. U.S. Pat. No. 3,251,897 describes alkylation of aromatic hydrocarbons in the presence of X- or Y-type crystalline aluminosilicate zeolites, specifically such type zeolites wherein the cation is rare earth and/or hydrogen. U.S. Pat. Nos. 3,751,504 and 3,751,506 describe vapor phase alkylation of aromatic hydrocarbons with olefins, e.g. benzene with ethylene, in the presence of a ZSM-5 type zeolite catalyst.

In these prior art processes, the xylene product produced has the equilibrium composition of approximately 24 percent para, 54 percent of meta and 22 percent of ortho.

The alkylation of toluene with methanol in the presence of a cation exchanged zeolite Y has been described by Yashima et al. in the Journal of Catalysis 16, 273-280 (1970). These workers reported selective production of para-xylene over the approximate temperature range of 200° to 275° C. with the maximum yield of para-xylene in the mixture of xylenes, i.e. about 50 percent of the xylene product mixture, being observed at 225° C. Higher temperatures were reported to result in an increase in the yield of meta-xylene and a decrease in the production of para- and ortho-xylene.

Transalkylation of toluene using a catalyst of faujasite or mordenite, a Group VIII metal, such as platinum, and an additional component of arsenic, antimony, bismuth, selenium, tellurium or compounds thereof is decribed in U.S. Pat. No. 3,527,824.

While the above-noted prior art is considered of interest in connection with the subject matter of the present invention, the conversion process described herein, utilizing a catalyst comprising a composite of a crystalline aluminosilicate zeolite and antimony trioxide, which zeolite has a silica/alumina ratio of at least about 12 and a constraint index within the approximate range of 1 to 12, has not, insofar as is known been heretofore described.

Of the xylene isomers, i.e. ortho, meta and paraxylene, meta-xylene is the least desired product, with ortho and para-xylene being the more desired products. Para-xylene is of particular value being useful in the manufacture of terephthalic acid which is an intermediate in the manufacture of synthetic fibers, such as "Dacron". Mixtures of xylene isomers, either alone or in further admixture with ethylbenzene, generally containing a concentration of about 24 weight percent para-xylene in the equilibrium mixture, have previously been separated by expensive superfraction and multistage refrigeration steps. Such process, as will be realized, has involved high operation costs and has a limited yield.

SUMMARY OF THE INVENTION

In accordance with the present invention, there has been discovered a process for the selective production of para-xylene by contacting, under conversion conditions, a charge stock containing as a major reactant, at least one hydrocarbon selected from the group consisting of toluene, a $C_3-C_{10}$ olefin, a $C_5-C_{10}$ naphthene, a $C_3-C_{10}$ paraffin, and mixtures thereof with one another with a catalyst comprising a crystalline aluminosilicate zeolite and antimony oxide. The crystalline aluminosilicate zeolite is essentially characterized by a silica to alumina ratio of at least about 12 and a constraint index within the approximate range of 1 to 12.

The present process comprises conversion of the specified hydrocarbons to yield xylenes in which the proportion of para-xylene isomer is substantially in excess of its normal equilibrium concentration and preferably in excess of 50 weight percent of the xylene product produced in the presence of the specified catalyst at a temperature between about 250° and about 800° C. at a pressure between about atmospheric and about 1000 psig utilizing a feed weight hourly space velocity (WHSV) between about 0.1 and about 2000. The latter WHSV is based upon the weight of catalyst composition, i.e. total weight of active catalyst and binder therefor. The effluent is separated and distilled to remove the desired products, e.g. para-xylene and unreacted product is recycled for further reaction.

DESCRIPTION OF SPECIFIC EMBODIMENTS

The charge stock utilized in the process of this invention contains as a major reactant, at least one hydrocarbon, which can be toluene, a $C_3-C_{10}$ olefin, $C_5-C_{10}$ naphthene such as cyclopentane alkylcyclopentane or cyclohexane, a $C_3-C_{10}$ paraffin such as butane or hexane and mixtures thereof with one another.

Typical of the processes contemplated herein are the disproportionation of toluene to benzene and xylenes, wherein the proportion of para-xylene obtained is greatly in excess of its normal equilibrium concentration. Such process is effectively carried out at a temperature of between about 400° and about 750° C at a pressure of between about 1 atmosphere and about 1000 psig utilizing a weight hourly space velocity of between about 1 and about 20.

Another process involves the methylation of toluene by reaction of the latter with a methylating agent, preferably methanol, at a temperature between about 250° C. and about 750° C. and preferably between about 400° C. and about 600° C. The reaction generally takes place at atmospheric pressure, but the pressure may be within the approximate range of 1 atmosphere to 1000 psig. The molar ratio of methylating agent to toluene is generally between about 0.05 and about 5. When methanol is employed as the methylating agent a suitable molar ratio of methanol to toluene has been found to be approximately 0.1–2 moles of methanol per mole of toluene. With the use of other methylating agents, such as methylchloride, methylbromide, dimethylether, methyl carbonate, light olefins, or dimethylsulfide, the molar ratio of methylating agent to toluene may vary within the aforenoted range. Reaction is suitably accomplished utilizing a weight hourly space velocity of between about 1 and about 2000 and preferably between about 5 and about 1500. The reaction product consisting predominantly of para-xylene or a mixture of para- and ortho-xylene, together with comparatively smaller amounts of meta-xylene may be separated by any suitable means, such as by passing the same through a water condenser and subsequently passing the organic phase through a column in which chromatographic separation of the xylene isomers is accomplished.

Another charge stock suitable for use in the process of the invention, is a stream high in $C_3$-$C_{10}$ olefin content. Thus, propylene, butenes, pentenes, hexenes, dienes such as butadiene, pentadienes, cycloolefins such as cyclopentene and cyclohexene, alkyl-substituted cycloolefins such as ethyl cyclopentene, cyclpentadiene and cyclohexadiene can be effectively converted to a high yield of para-xylene utilizing the described catalyst comprising a composite of a specified crystalline aluminosilicate zeolite and antimony oxide. Conversion utilizing such olefin feed is carried out at a temperature within the approximate range of 300° to 700° C., a pressure between atmospheric and 1500 psig employing a weight hourly space velocity between about 1 and about 1000.

As sources of the olefin reactant either substantially pure streams of the $C_3$-$C_{10}$ olefin may be employed or refinery or chemical streams high in such reactant, i.e. generally more than 50 volume percent may be used. It is also contemplated to employ a dual catalyst bed process utilizing an initial paraffin and/or naphtha feed. Insuch embodiment, a charge of $C_3$ to $C_{10}$ paraffins is conducted to a first catalyst bed containing a catalyst suitable for effecting conversion of the paraffin charge to olefins. The catalyst employed in such bed is a crystalline aluminosilicate zeolite of the type hereinafter described which has not been composited with antimony oxide, e.g. HZSM-5; HZSM-11; HZSM-12; HZSM-38 or HZSM-35. These zeolites may have combined therewith a small amount of phosphorus as described in copending application Ser. No. 508,308, filed Sept. 23, 1974 (now U.S. Pat. No. 3,972,832) or may have undergone prior steaming as described in copending application Ser. No. 538,665 filed Jan. 6, 1975 (now U.S. Pat. No. 3,965,209). Conditions present in such bed include a temperature within the approximate range of 400° to 750° C., a pressure between atmospheric and 1000 psig and a weight hourly space velocity of between about 0.5 and about 5000. The olefins formed in such operation are then passed through a second catalyst bed, maintained under conditions described hereinabove, containing the composite catalyst of crystalline aluminosilicate zeolite and antimony oxide, which zeolite has a silica to alumina ratio of at least about 12 and a constraint index within the approximate range of 1 to 12.

A still further charge stock which can be used in the process of the present invention to obtain high yields of para-xylene includes naphthenes, such as cyclopentane, cyclohexane and alkyl cyclopentanes having at least one alkyl group of 1 to 5 carbon atoms. Typical of the naphthene reactants are methyl cyclopentane, 1,2-dimethylcyclopentane, 1,3-dimethylcyclohexane. Another charge stock which can be effectively used in the present invention to selectively produce para-xylene includes paraffinic hydrocarbons having between 3 and 10 carbon atoms. Representative of such paraffins are butanes, pentanes, hexanes, heptanes, octanes and alkyl-substituted derivatives of these paraffins. Utilizing a paraffinic and/or naphthenic charge stock, reaction conditions include contact with the composite catalyst of crystalline aluminosilicate zeolite and antimony oxide at a temperature of between about 400° to about 700° C., a pressure between about atmospheric and about 1000 psig and a weight hourly space velocity of 0.1 to 100.

The catalysts utilized in the process of this invention comprise composites of antimony oxide and a crystalline aluminosilicate zeolite more fully described below. The antimony oxide is present as $Sb_2O_3$ alone or in admixture with other antimony oxides with or without metallic antimony or other antimony compounds being present. In all instances, regardless of the particular state of oxidation of the antimony, its content with respect to the zeolite is computed as if it were present as $Sb_2O_3$. Generally, the amount of $Sb_2O_3$ in the composite catalyst will be between about 6 and about 40 weight percent and preferably between about 10 and about 35 weight percent.

The catalyst of this invention may be a physical mixture of an antimony compound, preferably an oxide of antimony, e.g. $Sb_2O_3$ with the zeolite powder; or antimony metal powder; or the product formed by impregnation of the zeolite powder or pellets with one or more organic or inorganic antimony compound; or the product formed by any known catalyst preparation procedure that results in an intimate mixture. Antimony derivatives which may be used include: the hydrides $SbH_3$; the halides $MX_3$, $MX_5$ (M = Sb, X = F, Cl, Br, I); organic alkyl and aryl stibines and their oxides $R_3Sb$, $R_5Sb$, $R_xSb=O$ (R-alkyl or aryl); halogen derivatives $RSbX_2$, $R_2SbX$, $RSbX_4$, $R_2SbX_3$, $R_3SbX_2$, $R_4SbX$; the acids $H_3SbO_3$, $HSbO_2$, $HSb(OH)_6$; organic acids such as $RSbO(OH)_2$, $R_2SbO$ . OH, all with R and X defined as above noted. Also included are organic ethers such as $R_2SbOSbR_2$; esters and alcoholates such as $Sb(OOCCH_3)_3$, $Sb(OC_4H_9)_3$, $Sb(OC_2H_5)_3$, $Sb(OCH_3)_3$; and antimonyl salts as $(SbO)SO_4$, $(SbO)NO_3$, $K(SbO)C_4H_4O_6$, $NaSbO_2 . 3H_2O$. Binders such as clays silica, or other inorganic oxides may be used. When such are used, the total catalyst composition should preferably contain at least 50 percent by weight of crystalline aluminosilicate zeolite. When the catalyst composition has the desired physical form, it is dried and then calcined at a temperature of about 200° C. to about 600° C., preferably in an oxidizing atmosphere such as air. In some cases, calcining in a reducing atmosphere may be found preferable, in which case the calcining temperature should not exceed about 550° C.

The zeolite catalysts herein described are members of a novel class of zeolites exhibiting some unusual properties. These catalysts induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30. Such catalyst, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although puckered structures exist such as TMA offretite which is a known effective zeolie. Also, structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatrography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Catalysts suitable for the present invention are those having a constraint index in the approximate of 1 to 12. Constraint Index (CI) values for some typical catalysts are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10 and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F. to 950° F., the constraint index will have a value for any given zeolite of interest herein within the approximate range of 1 to 12.

The class of zeolites defined herein is exemplified by ZSM-5, ZSM-11, ZSM-12, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. application Ser. No. 528,060, filed Nov. 29, 1974, and now abandoned, and further described in continuation-in-part Ser. No. 560,412 filed Mar. 20, 1975, now U.S. Pat. No. 4,046,859 issued Sept. 6, 1977. This zeolite can be identified, in terms of mole ratios of oxides and in the anhydrous state, as follows:

$$(0.3-2.5)R_2O : (0-0.8)M_2O : Al_2O_3 : > 8\ SiO_2$$

wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4-2.5)R_2O : (0-0.6)\ M_2O : Al_2O_3 : xSiO_2$$

wherein R is an organic nitrogen-containing cation derived from a 2-(hydroxyalkyl)trialkylammonium compound, wherein alkyl is methyl, ethyl or a combination thereof, M is an alkali metal, especially sodium, and x is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33A.

TABLE I

| d(A) | $I/I_o$ |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity to 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| | Broad | Preferred |
|---|---|---|
| R+ + M+ | | |
| $R+ + M+$ | 0.2-1.0 | 0.3-0.9 |
| $OH^-/SiO_2$ | 0.05-0.5 | 0.07-0.49 |
| $H_2O/OH^-$ | 41-500 | 100-250 |
| $SiO_2/Al_2O_3$ | 8.8-200 | 12-60 | where R is an organic nitrogen-containing cation derived from a 2-(hydroxyalkyl) trialkylammonium compound and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and reovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in U.S. application Ser. No. 528,061, filed Nov. 29, 1974 and issued as U.S. Pat. No. 4,016,245 on Apr. 5, 1977. This zeolite can be identified, in terms of mole ratios of oxides and in the anhydrous state, as follows:

$$(0.3-2.5)R_2O : (0-0.8)M_2O : Al_2O_3 : > 8\ SiO_2$$

wherein R is an organic nitrogen-containing cation derived from ethylenediamine or pyrrolidine and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4-2.5)R_2O : (0-0.06)M_2O : Al_2O_3 : xSiO_2$$

wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3-11.5A. This very weak line, however, is determined not to be a significant line for ZSM-35.

TABLE II

| d(A) | $I/I_o$ |
|---|---|
| 9.6 ± 0.20 | Very Strong - Very Very Strong |
| 7.10 ± 0.15 | Medium |
| 6.98 ± 0.14 | Medium |

TABLE II-continued

| d(A) | I/I$_o$ |
|---|---|
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH$^-$/SiO$_2$ | 0.05–0.5 | 0.07–0.49 |
| H$_2$O/OH$^-$ | 41–500 | 100–250 |
| SiO$_2$/Al$_2$O$_3$ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 8 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000° F. for 1 hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilibite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

The catalysts of this invention may be in the hydrogen form or they may be base exchanged or impregnated to contain ammonium or a metal cation complement. It is desirable to calcine the catalyst after base exchange. The metal cations that may be present include any of the cations of the metals of Groups I through VIII of the Periodic Table. However, in the case of Group IA metals, the cation content should in no case be so large as to effectively inactivate the catalyst.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, −11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table including, by way of example, nickel, zinc, calcium or rare earth metals.

The crystals of zeolite in a form substantially free of alkali metal, i.e. containing less than about 1.5 weight percent alkali metal and preferably having at least a portion of the original cations associated therewith replaced by hydrogen of ammonium ion are then composited with an antimony compound. In general, it is contemplated that more than 50 percent and preferably more than 75 percent of the cationic sites of the crystalline aluminosilicate zeolite, above described, will be occupied by hydrogen ions. Preferred antimony compounds utilized in preparing the composite catalysts used in the process of the invention include antimony trimethoxide, antimony trioxide, and antimony metal powder, although other antimony sources as described hereinabove may be used.

The conversion process described herein may be carried out as a batch type, semi-continuous or continuous operation utilizing a fixed or moving bed catalyst system. The catalyst after use is conducted to a regeneration zone wherein coke is burned from the catalyst in an oxygen-containing atmosphere, e.g. air, at an elevated temperature, after which the regenerated catalyst is recycled to the conversion zone for further contact with the charge stock.

The following examples will serve to illustrate the process of the invention without limiting the same:

EXAMPLE 1

A catalyst composition was prepared by mixing one part of $Sb_2O_3$ with 2.3 parts of HZSM-5. The resulting mixture was pelleted and sieved to 8/14 mesh. The particles so obtained were conditioned in nitrogen (50 cc/minute flow rate) for 3 hours at 525° C. and thereafter calcined in air for 0.5 hour at 525° C. The catalyst contained 30 weight percent $Sb_2O_3$ in combination with HZSM-35.

EXAMPLE 2

The catalyst described in Example 1 was used for disproportionation of toluene by passing over 1 gram of the catalyst at 550° C. at a weight hourly space velocity of 1. The catalyst was calcined in air for 20 hours at 500° C. after approximately 6 hours on stream. The conditions and results are shown in Table I below.

TABLE I

| Hours On Stream | Toluene Conversion, Mole % | Mole % Selectivity Benzene | Mole % Selectivity Xylenes | % Para of Xylene Product |
|---|---|---|---|---|
| 6.7 | 6.8 | 3.9 | 2.9 | 91.9 |
| 8.0 | 8.9 | 4.8 | 4.1 | 80.7 |
| 9.2 | 14.0 | 7.6 | 6.4 | 72.0 |
| 10.7 | 17.5 | 9.5 | 8.0 | 62.3 |
| 12.2 | 16.4 | 8.8 | 7.6 | 58.0 |
| 14.1 | 12.2 | 6.4 | 5.8 | 56.5 |
| 15.5 | 8.8 | 4.7 | 4.1 | 58.5 |
| Calcined for 64 Hours in Air at 500° C. | | | | |
| 16.8 | 6.3 | 3.5 | 2.8 | 100 |
| 18.0 | 9.5 | 5.2 | 4.1 | 93.5 |
| 19.8 | 10.9 | 5.8 | 5.1 | 88.4 |
| 21.2 | 12.7 | 6.8 | 5.9 | 86.2 |
| 22.8 | 11.8 | 6.3 | 5.5 | 83.9 |
| 24.3 | 9.5 | 5.1 | 4.5 | 82.9 |
| 25.8 | 8.8 | 4.7 | 4.1 | 81.4 |
| 27.3 | 7.0 | 3.75 | 3.2 | 80.8 |

EXAMPLE 3

A catalyst prepared similar to that of Example 1, but utilizing 3 parts of HZSM-5 rather than 2.3 parts, was treated in air under static conditions (non-flowing) for 44 hours at 550° C. and used for disproportionation to toluene. The catalyst contained 25 weight percent $Sb_2O_3$. The toluene charge was passed over 2 grams of the catalyst at 550° C. at a weight hourly space velocity of 3.1. The conditions and results are shown in Table II below.

TABLE II

| Hours On Stream | Toluene Conversion, Mol % | Mole % Selectivity Benzene | Mole % Selectivity Xylenes | % Para of Xylene Product |
|---|---|---|---|---|
| 2.0 | 5.7 | 3.15 | 2.3 | 90.3 |
| 3.0 | 6.2 | 3.4 | 2.5 | 90.3 |
| 4.0 | 9.4 | 5.0 | 3.7 | 85.2 |
| Calcined in Air (50 cc/minute) for 24 Hours at 550° C. | | | | |
| 6.0 | 1.8 | 1.1 | 0.7 | 100 |
| 7.0 | 2.2 | 1.2 | 1.0 | 100 |
| 8.0 | 2.5 | 1.4 | 1.1 | 100 |
| 10.0 | 3.0 | 1.6 | 1.3 | 100 |

EXAMPLE 4

6.5 grams of antimony trimethoxide $Sb(CH_3O)_3$ dissolved in 75 cc of para-xylene were refluxed with 10 grams of HZSM-5 for 16 hours. The mixture was cooled, filtered and the filter cake washed with 100 cc of toluene, then 100 cc of methanol, then 100 cc of pentane, after which it was dried in air. The solids were then vacuum dried at 115° C. for 3 hours, and formed into pellets without a binder. The pellets were then calcined in air at 300° C. for 1 hour. The catalyst contained 24 weight percent antimony as $Sb_2O_3$.

EXAMPLE 5

Using the catalyst of Example 4, toluene was disproportionated by passing over 2 grams of such catalyst at a temperature of 500°, 550° and 600° C. The conditions and results are shown in Table III below.

TABLE III

| Temp °C | WHSV | Toluene Conversion, Mol % | Selectivity Benzene (Moles) | Selectivity P-Xylene (Moles) | Xylenes Para/ | Xylenes Metal/ | Xylenes Ortho |
| --- | --- | --- | --- | --- | --- | --- | --- |
| 500 | 13 | 0.5 | .275 | .2 | 100** | | |
| 550 | 13 | 1.0 | .56 | .34 | 100** | | |
| 550 | 3.1 | 2.6 | 1.67 | 0.9 | 73.9 | 18.3 | 7.6 |
| *550 | 13+1.6H$_2$O | 0.7 | .44 | .20 | 100** | | |
| 550 | 1.4 | 2.0 | 1.28 | 0.7 | 75.5 | 17.8 | 6.6 |
| 600 | 1.4 | 5.2 | 3.34 | 1.8 | 70.5 | 21.2 | 8.2 |
| | | Calcine at 600° C. for 16 Hours. | | | | | |
| 600 | 1.4 | 5.5 | 4.06 | 1.3 | | | |

*Charge was toluene and water
**Estimated - Within limits of accuracy of instrument

EXAMPLE 6

A catalyst composition was prepared by mixing, in finely divided form, 1.23 grams of Sb$_2$O$_3$ with 5 grams of HZSM-5. The resulting mixture was pressed into a cake, crushed, sieved to 8/14 mesh size and thereafter calcined 1 hour in air at 500° C. The catalyst contained 20 weight percent Sb$_2$O$_3$ in combination with HZSM-5.

EXAMPLE 7

The catalyst described in Example 6 was used for disproportionating toluene by passing over 2 grams of the catalyst at a temperature of 500° C. and 550° C. The conditions and results are shown in Table IV below.

TABLE IV

| Temp °C | WHSV | Toluene Conversion, Mol % | Selectivity, % Benzene | Selectivity, % Xylenes | % Para of Xylene Product |
| --- | --- | --- | --- | --- | --- |
| 500 | 1.2 | 4.9 | 3.6 | 1.3 | 56.9 |
| 550 | 11.3 | 0.9 | 0.6 | 0.3 | 84.8 |
| 550 | 1.2 | 4.0 | 2.8 | 1.2 | 51.3 |
| 550 | 1.2 | 4.6 | 2.8 | 1.8 | 51.4 |

EXAMPLE 8

A 2 gram sample of the catalyst described in Example 4 was loaded into a reactor and a mixture of toluene and methanol (4 to 1 molar ratio) was contacted with the catalyst at temperatures in the range of 400° to 550° C. The conditions and results are shown below in Table V below.

TABLE V

| Temp °C | WHSV | Toluene Conversion, Mol % | % Xylenes In Aromatics Product | % Para Xylene (In Xylenes) |
| --- | --- | --- | --- | --- |
| 400 | 12.2 | 5.3 | 85.7 | 84.4 |
| 500 | 12.2 | 14.6 | 90.2 | 89.9 |
| 550 | 12.2 | 29.2 | 91.1 | 90.5 |
| 550 | 3.7 | 34.4 | 89.6 | 80.1 |
| 550 | 12.2 | 27.8 | 90.8 | 94.9 |

From the above results, it will be seen that there was a highly selective production of para-xylene utilizing the catalyst composite of HZSM-5 and antimony oxide.

EXAMPLE 9

A 2 gram sample of the catalyst described in Example 6 was loaded into a reactor and a mixture of toluene and methanol (4 to 1 molar ratio) was contacted with the catalyst at 550° C. at a weight hourly space velocity of 3.8. The conversion of toluene was 42 percent and the amount of xylenes contained in the aromatics product was 84.8 percent, with the percentage of para-xylene of the xylene produced being 52.1.

EXAMPLE 10

A 2 gram sample of the catalyst described in Example 4 was loaded into a reactor and isobutene was passed over the catalyst at a temperature of about 400°–500° C., 1 atmosphere pressure and a weight hourly space velocity of 2–4.

The products found were collected and analyzed with the following results:

| Gas, Wt.% | |
| --- | --- |
| Methane | 1 |
| Ethane | 1 |
| Ethylene | 20 |
| Propane | 7 |
| Propylene | 45 |
| Butane | 15 |
| Butylenes | 2 |
| C$_5$'s | 9 |
| Liquid, Wt.% | |
| Benzene | 5.5 |
| Toluene | 31 |
| Xylenes | 36 (para/meta/ortho = 93/5/2) |
| p-Ethyl Toluene | 11 |
| Ethylbenzene | 5.5 |
| 1,2,4-trimethyl-benzene | 3 |
| Others | 8 |

EXAMPLE 11

A catalyst composition was prepared by mixing, in finely divided form, 3 parts by weight of Sb$_2$O$_3$ with 7 parts by weight of HZSM-5. The resulting mixture was pressed into a cake, crushed, sieved to 8/14 mesh size and thereafter heated in nitrogen for 3 hours at 525° C. followed by heating in air for 3 hours at 525° C. The catalyst contained 30 weight percent Sb$_2$O$_3$ in combination with HZSM-5.

EXAMPLE 12

The catalyst described in Example 11 was used for aromatization of propylene by passing the latter over 1 gram of the catalyst contained in a reactor of approximately 15 cm. length and approximately 14 mm. in diameter. Prior conditioning of the catalyst was effected by heating the catalyst to 525° C. over 1 hour in 50 cc/minute flowing nitrogen, holding in nitrogen for 3 hours at 500°–525° C., followed by air (50 cc/minute) for 0.5 hour. Reaction conditions included a temperature in the range of 400° C. to 525° C. and a weight hourly space velocity in the range of 1 to 12. Such conditions, together with the results obtained are shown in Table VI below.

TABLE VI

| Run No. | 1 | 2 | 3 | 4 | 5 | 6 | 7 | 8 | 9 | 10 | 11 | 12 |
| --- | --- | --- | --- | --- | --- | --- | --- | --- | --- | --- | --- | --- |

TABLE VI-continued

| Temp, °C | 400 | 400 | 400 | 400 | 400 | 400 | 400 | 425 | 450 | 475 | 500 | 525 |
|---|---|---|---|---|---|---|---|---|---|---|---|---|
| WHSV | 3.0 | 3.0 | 6.0 | 12.0 | 1.0 | 3.0 | 3.0 | 3.0 | 3.0 | 3.0 | 3.0 | 3.0 |
| Hrs. on Stream | 0.5 | 1.5 | 3.2 | 4.4 | 5.7 | 6.8 | 8.2 | 9.75 | 10.9 | 12.25 | 13.75 | 15.2 |
| Products, Wt % | | | | | | | | | | | | |
| ALIPHATICS | | | | | | | | | | | | |
| Ethylene | * | 2.21 | * | * | 1.85 | 2.40 | * | * | 4.46 | 6.07 | 8.78 | 10.36 |
| Ethane | | .47 | | | .62 | .23 | | | .83 | .93 | 1.34 | 1.07 |
| Propylene | | 6.00 | | | 4.99 | 9.19 | | | 11.59 | 14.57 | 18.45 | 23.20 |
| Propane | | 11.09 | | | 12.60 | 7.37 | | | 11.2 | 11.90 | 11.82 | 8.72 |
| Butane | | 18.00 | | | 20.63 | 11.77 | | | 13.56 | 11.95 | 9.00 | 5.76 |
| Butenes | | 16.19 | | | 7.96 | 16.18 | | | 13.67 | 14.81 | 14.81 | 16.57 |
| $C_5^+$ | | 21.76 | | | 26.28 | 34.53 | | | 21.49 | 18.62 | 13.61 | 13.28 |

Air regen. 500° C/2 hrs (after Run No. 6)

| Run No. | 1 | 2 | 3 | 4 | 5 | 6 | 7 | 8 | 9 | 10 | 11 | 12 |
|---|---|---|---|---|---|---|---|---|---|---|---|---|
| Temp, °C | 400 | 400 | 400 | 400 | 400 | 400 | 400 | 425 | 450 | 475 | 500 | 525 |
| WHSV | 3.0 | 6.0 | 12.0 | 1.0 | 3.0 | 3.0 | 3.0 | 3.0 | 3.0 | 3.0 | 3.0 | 3.0 |
| Hrs. on Stream | 0.5 | 1.5 | 3.2 | 4.4 | 5.7 | 6.8 | 8.2 | 9.75 | 10.9 | 12.25 | 13.75 | 15.2 |
| Products, Wt % | | | | | | | | | | | | |
| AROMATICS | | | | | | | | | | | | |
| Benzene | 8.0 | 1.22 | 4.3 | 3.6 | 1.09 | 1.40 | 3.5 | 4.1 | 1.42 | 1.54 | 1.97 | 2.09 |
| Toluene | 21.4 | 6.99 | 26.5 | 18.75 | 8.12 | 3.93 | 21.1 | 27.5 | 8.00 | 7.76 | 8.96 | 8.73 |
| Ethylbenzene | 6.2 | 1.30 | 6.0 | 4.6 | 1.33 | .78 | 6.0 | 6.9 | 1.5 | 1.46 | 1.38 | 1.28 |
| Xylenes | 35.7 | 9.00 | 35.9 | 9.14 | 6.67 | 32.4 | 39.6 | 8.84 | 7.91 | 7.90 | 7.22 | |
| Paraethyltoluene | 17.7 | 3.99 | 17.5 | 20.7 | 3.56 | 3.55 | 18.4 | 15.3 | 2.45 | 1.67 | 1.20 | 1.08 |
| Diethylbenzene | 6.9 | 0.90 | 5.4 | 8.1 | 0.75 | 1.02 | 5.5 | 3.5 | 0.48 | 0.34 | 0.27 | 0.24 |
| Other | 4.1 | 0.88 | 4.4 | 8.5 | 1.07 | 0.98 | 13.1 | 3.1 | 0.4 | 0.47 | 0.51 | 0.40 |
| Total Aromatics | 27.5 | 24.28 | 16.8 | 8.4 | 25.07 | 18.33 | 19.6 | 24.1 | 23.08 | 21.15 | 22.19 | 21.04 |
| Para in Xylenes | 97.18 | 97.7 | 97.6 | 95.1 | 88.0 | 94.3 | 96.9 | 95.9 | 93.8 | 85.3 | 76.7 | 74.8 |
| $C_3=$ Conversion | >90 | 94.0 | | | 95.11 | 90.81 | | | 88.41 | 85.43 | 81.55 | 76.80 |

*Liquid only analyzed for aromatics selectivity

From the above results, it will be seen that at 400° C., para-xylene selectively was about 96 percent and such was not affected by varying the space velocity from 3 to 12. With increasing severity (lower WHSV) toluene yields increased at the expense of para-ethyltoluene and para-diethylbenzene. The major effect of product selectivity was attributable to change in reaction temperature. Propylene conversion and para-xylene selectivity decreased with increasing temperature. Toluene selectivity increased at the expense of para-ethyltoluene and para-diethylbenzene with an increase in temperature. The yield of ethylene from propylene increased from about 2.5 weight percent at 400° C. to about 10 weight percent at 525° C.

EXAMPLE 13

A catalyst prepared as in Example 3 was used for aromatization of propylene.

A summary of the results obtained at a weight hourly space velocity of 0.5 and 3 and a temperature of 550° C. and 600° C. are shown below in Table VII.

TABLE VII

| Temp. | 550° C. | | 600° C. | |
|---|---|---|---|---|
| WHSV | 3 | 0.5 | 3 | 0.5 |
| $C_2H_4$ | 11 | 10 | 24 | 20 |
| $C_2-C_4$ Paraffins | 38 | 30 | 18 | 15 |
| $C_4H_8$ | 8 | 4 | 16 | 7 |
| $C_5^+$ | 7 | 2.6 | 5.9 | 3.3 |
| Methane | ~0 | ~0 | 5 | 5 |
| Benzene | 5 | 11.5 | 8.5 | 14 |
| Toluene | 16 | 24 | 13 | 21 |
| Xylenes | 12 | 14 | 8 | 11 |
| Ethylbenzene | 1.5 | 1.3 | 1.2 | 1.3 |
| $C_9^+$ | 1.5 | 2.6 | 0.4 | 2.4 |
| $C_3H_6$ Conversion | 88 | 91 | 75 | 78 |
| % Para in Xylenes | 64 | 31 | 65 | 37.5 |
| Total Aromatics | 36 | 53.4 | 31.1 | 49.7 |

EXAMPLE 14

A catalyst prepared as in Example 3 was used for conversion of various hydrocarbons including propylene, butane, butene, propane and hexane by passing over 2 grams of such catalyst at a temperature of 500°-600° C. at a weight hourly space velocity within the range of 0.5 to 3.8. The charge and reaction conditions are shown in Table VIII below.

TABLE VIII

| Run No. | Time on Stream (Hrs.) | Feed Charge | WHSV | Temp °C. |
|---|---|---|---|---|
| 1 | 1.5 | Propylene | 3.0 | 500 |
| 2 | 2.9 | Propylene | 0.5 | 500 |
| 3 | 4.8 | n-Butane | 3.8 | 500 |
| 4 | 6.2 | 1-Butene | 3.6 | 500 |
| 5 | 7.5 | Propane | 3.2 | 500 |
| 6 | 9.0 | n-Hexane | 0.7 | 500 |
| Calcined at 500° C. in Air (50 cc/min) for 0.5 Hr.; Then at 550° C. in Air for 67 Hrs. | | | | |
| 7 | 10.8 | Propylene | 3.0 | 500 |
| 8 | 12.1 | Propylene | 0.5 | 500 |
| 9 | 13.4 | Propylene | 3.0 | 550 |
| 10 | 14.7 | Propylene | 0.5 | 550 |
| 11 | 16.2 | Propylene | 3.0 | 600 |
| 12 | 17.7 | Propylene | 0.5 | 600 |
| 13 | 19.7 | Propylene | 3.0 | 600 |
| Calcined in Air at 550° C. Overnight. | | | | |
| 14 | 21.0 | n-Butane | 0.5 | 550 |
| 15 | 23.0 | n-Butane | 0.5 | 550 |
| 16 | 24.8 | n-Butane | 0.5 | 550 |

The results obtained for Runs 3, 4, 5, 6 and 15 wherein the feed was n-butane, 1-butene, propane, n-hexane and n-butane respectively are set forth below in Table IX.

TABLE IX

| Products, Wt. % | Run 3 n-Butane | Run 4 1-Butene | Run 5 Propane | Run 6 n-Hexane | Run 15 n-Butane |
|---|---|---|---|---|---|
| Ethylene | 12.8 | 7.9 | 57.3 | 9.6 | 10.6 |
| Ethane | 11.5 | 1.0 | 0 | 3.0 | 20.7 |
| Propylene | 15.8 | 15.7 | 0 | 38.9 | 7.9 |
| Propane | 30.7 | 13.1 | — | 0 | 28.0 |
| Butene | 14.8 | 5.4 | 6.3 | 9.6 | 3.6 |
| Butanes | 5.75 | 7.4 | 14.1 | 3.1 | 1.9 |
| $C_5^+$ | 3.6 | 14.75 | 8.7 | 4.5 | 0.9 |
| Aromatics | 5.1 | 27.2 | 13.6 | 31.3 | 26.5 |
| Para in Xylenes | ~100 | 72.0 | ~100 | 63.6 | 41.5 |
| Conversion | 12.5 | 93 | 1.4 | 30.1 | 80.4 |

From the above results, it will be seen that selectivity to para-xylene production in every instance exceeded equilibrium concentration and in the case of Runs 3 and 5 approximated 100 percent.

EXAMPLE 15

A catalyst composition was prepared by mixing, in finely divided form, 1 part by weight of $Sb_2O_3$ with 3 parts by weight of HZSM-5. The resulting mixture was sieved to 8/14 mesh and thereafter heated for 2 hours in air at 550° C. The catalyst contained 25 weight percent $Sb_2O_3$ in combination with HZSM-5.

EXAMPLE 16

A 2.0 gram sample of the catalyst described in Example 15 was loaded into a reactor and cyclopentane was passed over the catalyst at temperatures of 400°, 450° and 500° C., 1 atmosphere pressure and a weight hourly space velocity of 3.36.

The liquid products formed were collected and analyzed with the results shown below in Table X.

TABLE X

| Temp °C | Cyclopentane Conversion, % | * | Benzene | Toluene | Ethyl Benzene | Xylene Para | Xylene Meta | Xylene Ortho | Para-Ethyl Toluene | Pseudo-Cumene | Durene |
|---|---|---|---|---|---|---|---|---|---|---|---|
| 400 | 10 | 36 | 3.2 | 16.8 | 2.6 | 5.8 | 7.4 | 2.8 | 0.8 | 9.0 | 0.6 |
| | | | | | | \[para/meta/ortho = 36.3/45.9/17.8\] | | | | | |
| 450 | 12 | 38 | 5.7 | 18.7 | 3.0 | 15.3 xylenes | | | 0 | 5.9 | 0 |
| | | | | | | \[para/meta/ortho = 34.2/46.8/19.0\] | | | | | |
| 500 | 97 | 1.5 | 13.4 | 41.9 | 2.6 | 28.2 xylenes | | | 1.0 | 2.6 | 1.0 |
| | | | | | | \[para/meta/ortho = 25.2/51.3/335.\] | | | | | |

*Liquid product with a lower boiling point than cyclopentane

From the above results it will be seen that at a temperature of 400° and 450° C., para-xylene selectivity was 34–36 percent. At 500° C. there was a very marked increase in reactivity, with approximately the equilibrium concentration of p-xylene being produced.

EXAMPLE 17

The same catalyst used in Example 16 was employed after calcining in air for 2 hours at 550° C. and methylcyclopentane was passed thereover at temperatures of 400°, 450° and 500° C., 1 atmosphere pressure and a weight hourly space velocity of 3.3.

The liquid products formed were collected and analyzed with the results shown below in Table XI.

TABLE XI

| Temp °C | Methylcyclo-Pentane, Conv.% | * | Benzene | Toluene | Ethyl Benzene | Xylenes | Para-Ethyl Benzene | Psuedo-Cumene | Durene |
|---|---|---|---|---|---|---|---|---|---|
| 400 | 13 | 24.7 | 4.0 | 14.8 | 1.8 | 9.2 | 2.8 | 28.0 | |
| | | | | | | \[para/meta/ortho = 62/27.8/10.2\] | | | |
| 450 | 9 | 22 | 13.9 | 14.0 | 1.8 | 7.7 | 3.2 | 5.7 | 0.6 |
| | | | | | | \[para/meta/ortho = 67.4/24.5/8.1\] | | | |
| 500 | 14 | 13 | 30 | 21.4 | 2.6 | 11.2 | 3.3 | 3.2 | 0.9 |
| | | | | | | \[para/meta/ortho = 62.5/26.4/11.1\] | | | |

*Liquid product with boiling point less than methylcyclopentane

From the above results, it will be seen that the para-xylene selectivity in the xylenes produced was considerably higher when methylcyclopentane rather than cyclopentane was employed as the charge.

It is to be understood that the foregoing description is merely illustrative of preferred embodiments of the invention of which many variations may be made by those skilled in the art within the scope of the following claims without departing from the spirit thereof.

I claim:

1. A process for the selective production of paraxylene which comprises contacting a stream containing more than 50 volume percent of $C_3 - C_{10}$ olefin at a temperature within the approximate range of 300° to 700° C, a pressure between atmospheric and 1500 psig, at a weight hourly space velocity between about 1 and about 1000 with a catalyst consisting essentially of a composite of a crystalline aluminosilicate zeolite and between about 6 and about 40 weight percent of antimony oxide, said zeolite having a silica to alumina ratio of at least about 12 and a constraint index within the approximate range of 1 to 12, collecting the resulting product and separating para-xylene therefrom.

2. The process of claim 1 wherein said stream is substantially pure $C_3 - C_{10}$ olefin.

3. The process of claim 1 wherein said olefin is propylene.

4. The process of claim 1 wherein said olefin is isobutene or 1-butene.

5. The process of claim 1 wherein said olefin is derived from catalytic conversion of a paraffin or naphtha feed.

6. The process of claim 1 wherein said crystalline aluminosilicate zeolite is ZSM-5.

7. The process of claim 1 wherein said crystalline aluminosilicate zeolite is HZSM-5.

8. The process of claim 1 wherein the amount of antimony oxide in said catalyst is between about 10 and about 35 percent.

* * * * *

UNITED STATES PATENT AND TRADEMARK OFFICE
CERTIFICATE OF CORRECTION

PATENT NO. : 4,080,396

DATED : March 21, 1978

INVENTOR(S) : STEPHEN A. BUTTER

It is certified that error appears in the above-identified patent and that said Letters Patent are hereby corrected as shown below:

Column 11, Table, "all numbers under cc/cc of the second column" should read under the third column --Framework Density--.

Column 12, line 32, "to" should read --of--.

Column 13, line 17, "1,23" should read --1.23--.

Column 16, Table VI, Run 9, in the Propane Column under Run 9 "11.2" should read --11.32--.

Column 15, Table VI, Run 2, (second half of table) in the WHSV column, under Run 2 "6.0" should read --3.0--.

Column 15, Table VI, Run 3, WHSV Column, Run 3, "12.0" should read --6.0--.

Column 15, Table VI, Run 4, WHSV Column, Run 4, "1.0" Should read --12.0--.

Column 15, Table VI, Run 4, Xylenes (Aromatics), Run 4, "9.14" should read --35.7--.

Column 15, Table VI, Run 5, WHSV Column, Run 5, "3.0" should read --1.0--.

Column 15, Table VI, Run 6-12, Xylenes - change "32.4" should read --6.67-- in Run 6 and then move 32.4 into Run 7 (under Xylenes). Do this all the way through Run 11, Each number has to be moved into the next run.

Column 16, Table VI, Run 9, Ethylbenzene, "1.5" should read --1.35--.

UNITED STATES PATENT AND TRADEMARK OFFICE
CERTIFICATE OF CORRECTION

PATENT NO. : 4,080,396

DATED : March 21, 1978

INVENTOR(S) : STEPHEN A. BUTTER

It is certified that error appears in the above-identified patent and that said Letters Patent are hereby corrected as shown below:

Column 16, Table VI, Run 9, other "0.4" should read --0.54--.
Column 18, Table X, last line of table
"[para/meta/ortho = 25.2/51.3/335.]"
should read --[para/meta/ortho = 25.2/51.3/33.5]--.

Signed and Sealed this

Seventeenth Day of October 1978

[SEAL]

Attest:

RUTH C. MASON
Attesting Officer

DONALD W. BANNER
Commissioner of Patents and Trademarks